(12) United States Patent
Zamoyski

(10) Patent No.: US 6,468,247 B1
(45) Date of Patent: Oct. 22, 2002

(54) PERFUSION DEVICE FOR LOCALIZED DRUG DELIVERY

(76) Inventor: Mark Zamoyski, 988 Foothill Dr., San Jose, CA (US) 95123

( * ) Notice: Subject to any disclaimer, the term of this patent is extended or adjusted under 35 U.S.C. 154(b) by 0 days.

(21) Appl. No.: 09/557,188

(22) Filed: Apr. 21, 2000

(51) Int. Cl.[7] .............................................. A61M 37/00
(52) U.S. Cl. .......................................... 604/131; 606/1
(58) Field of Search ................................ 604/191, 173, 604/131; 606/1

(56) References Cited

U.S. PATENT DOCUMENTS

| | | | | |
|---|---|---|---|---|
| 2,670,673 A | * | 3/1954 | Gordon et al. | 604/173 |
| 3,467,096 A | * | 9/1969 | Horn | 604/173 |
| 4,744,981 A | | 5/1988 | Pavanasasivam | |
| 4,795,441 A | * | 1/1989 | Bhatt | 128/DIG. 26 |
| 4,846,797 A | * | 7/1989 | Howson et al. | 128/DIG. 1 |
| 4,906,452 A | | 3/1990 | Sivam | |
| 5,243,982 A | * | 9/1993 | Mostl et al. | 128/DIG. 12 |
| 5,417,683 A | * | 5/1995 | Shiao | 604/173 |
| 5,860,957 A | * | 1/1999 | Jacobsen et al. | 604/140 |

* cited by examiner

Primary Examiner—Edward K. Look
Assistant Examiner—Kimya N McCoy

(57) ABSTRACT

A device for localized delivery of drugs into a user definable, three dimensional area within a tissue mass comprising a means for securely housing a plurality of hypodermic needles, a means of impaling and retracting the hypodermics into a tissue mass, and a means of injecting the contents of the hypodermics as they are being retracted.

2 Claims, 6 Drawing Sheets

PERFUSION DEVICE FOR LOCALIZED DRUG DELIVERY

BACKGROUND—FIELD OF INVENTION

This invention relates generally to devices and methods for drug delivery, and more specifically devices for facilitating the use of hypodermic needles. The device of current invention provides means for uniform, localized drug delivery into a user definable, three dimensional area within a tissue mass.

BACKGROUND—DESCRIPTION OF PRIOR ART

Localized administration of certain drugs can allow much greater concentrations to be administered into the area targeted for treatment while at the same time reducing unwanted systemic effects or systemic cytotoxicity. Chemotherapeutics are one example of such a class of drugs. Device of present invention provides means for uniform, localized administration of such drugs, when feasible, directly into target cell populations and surrounding tissue. More specifically, device of current invention provides a means of delivering a plurality of hypodermic injections simultaneously so that the resulting perfusion of the drug occurs uniformly over a three dimensional area.

OBJECTS OF INVENTION

It is an object of the invention to provide an apparatus and method for localized, uniform perfusion of drugs to an area targeted for treatment.

It is an object of the invention to provide a method of administering chemotherapeutics which results in greater efficacy and lower systemic cytotoxicity.

It is an object of current invention to provide means to utilize certain drugs that heretofore were not usable because of complications resulting from oral administration or injection into general circulation.

It is an object of current invention to provide a minimally invasive "chemo surgery" procedure for ablation of unwanted or malignant tissue.

It is an object of current invention to provide a means for administering high dose chemotherapy to target cell populations without the need for bone marrow transplantation.

It is an object of current invention to provide a non surgical, non disfiguring, method of treating breast cancer and other cancers.

SUMMARY OF INVENTION

In accordance with the invention a three mechanism device, the first mechanism with means for securely seating a plurality of hypodermic needles, a second mechanism with means of impaling and retracting said hypodermics into a tissue mass, and a third mechanism with means of injecting the contents of said hypodermics while said hypodermics are being retracted.

STATIC DESCRIPTION OF INVENTION

Figure 1:
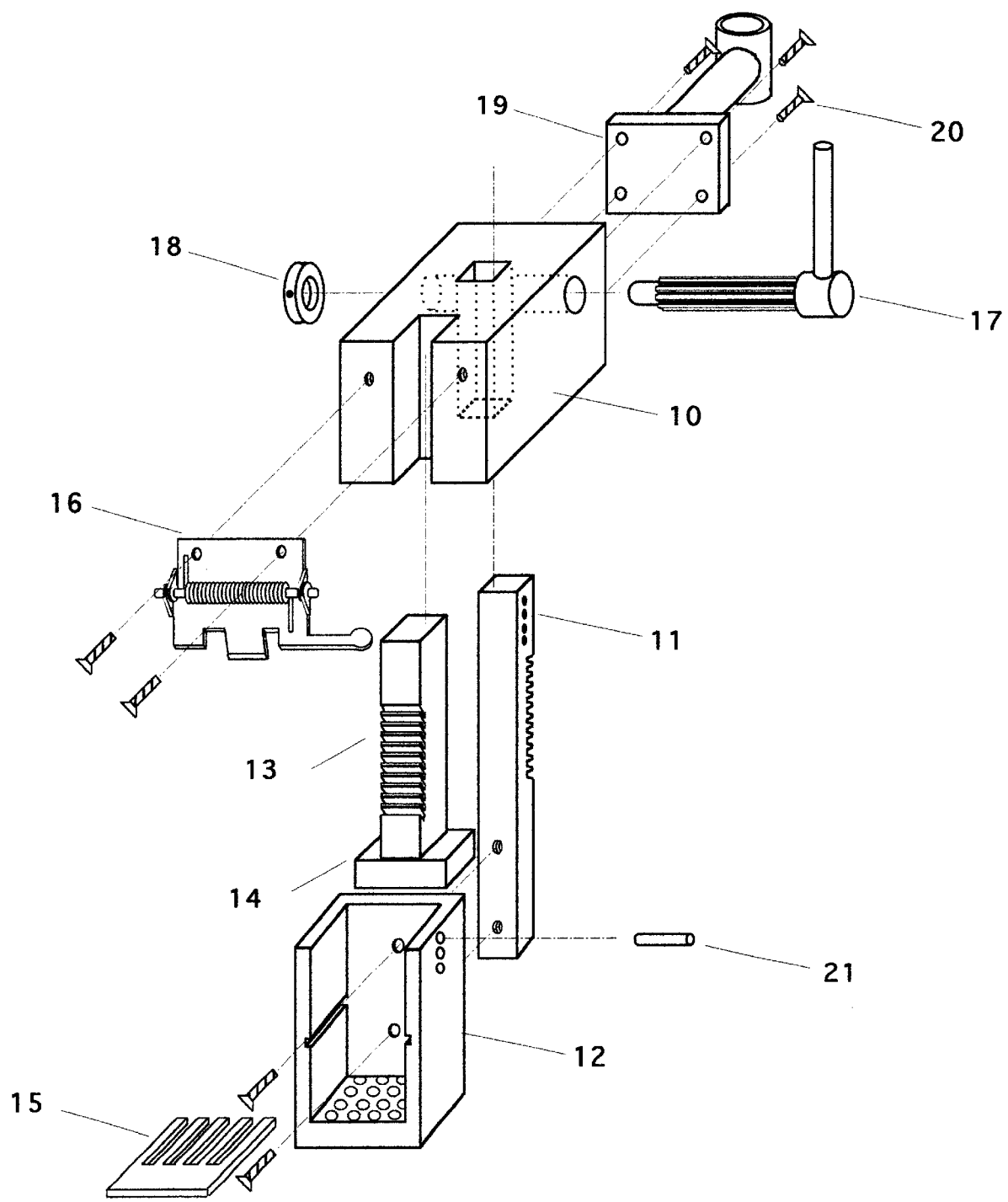
FIG. 1 is a perspective view illustrating the preferred embodiment of the device.

In accordance with the preferred embodiment of the present invention FIG. 1 shows a device comprised of a hypodermic chamber 12 and slidable element 15 capable of seating and securing a plurality of hypodermic needles attached to a means of lowering and raising the chamber 11, 17 and means of injecting 13,14,16 the contents of said hypodermic needles. Also shown is an attachment means 19 for attaching the main body 10 of the device to a means of positioning device relative to a patient.

The preferred embodiment of the hypodermic chamber 12 has a floor member in which holes or orifices are drilled to match the geometry of hypodermic needles to be used so that the said hypodermics fit snugly into the holes. Three walls extend upward from the floor member. The preferred embodiment shows a groove in two of the walls capable of accepting a slidable element 15 however there may be a plurality of grooves at varying height in the walls, the groove(s) may extend around all three walls, or the walls may not have grooves but instead use a lip or any other suitable means or hardware for accepting the slidable element 15. The slidable element is a substantially planar and rectangular piece of plastic or metal into which a plurality or parallel, linear cuts have been made or routed from one side to result in a plurality of finger like projections from one side. On or more of the walls may also have a plurality of holes drilled so that a peg 21 may be inserted through said holes after the planar part 14 of the injector arm 13,14 has been inserted into the chamber 12 however any other suitable hardware or means may be used to make sure the injector arm 13,14 travels downward with the chamber. Preferred embodiment shows hypodermic chamber 12 attached to impalement/retraction rack 11 by fasteners however any suitable hardware or means of readily attaching and detaching the chamber 12 to impalement/retraction rack 11 may be used. Alternatively, a suitable housing may be attached to impalement/retraction rack allowing the hypodermic chamber 12 to be snapped in or out, slid in or out, or readily attached or detached by any suitable means. The preferred embodiment shows a three walled substantially rectangular hypodermic chamber 12 however any suitable geometry may be used and a chamber made up of only two walls extending upward may also be used (shown in FIG. 3 and described later). The hypodermic chamber 12 may also employ a removable floor that may be readily interchanged with a different floor. The hypodermic chamber 12 floor may also be capable of accepting adapters in the holes to allow a different style or diameter of hypodermic to be used or to alter the depth of how the hypodermic is seated so that the length of the needles protruding from the bottom of the chamber may be varied to achieve a variable contour of the protruding needles. Although the preferred embodiment shows the hypodermic chamber 12 with means of accepting a plurality of hypodermics alternate embodiments envisioned could be used with a single large diameter hypodermic which has a plurality of needles at one end, a bladder with a plurality of needles at one end, or any other suitable injecting device currently existing or to be developed in the future.

The means of lowering and raising the chamber in the preferred embodiment is comprised of a impalement/retraction rack 11 and pinion gear 17 which is housed in the main body 10 of the device however a screw drive or any other suitable means of lowering and raising the hypodermic chamber 12 could be used. The impalement/retraction rack 11 shown also has a plurality of holes drilled through its upper part so that when the impalement/retraction rack 11 is housed in the main body 10 a peg such as 21 or pin can be inserted through one of the holes to act as a depth stop, preventing the rack from traveling lower then a user determined point however any other suitable hardware or means of restricting the amount of downward travel may be used or alternatively no means of depth control may be employed. The pinion gear 17 shown is lever operated however any other suitable means of providing rotation force to the pinion gear may be substituted. The pinion gear 17 is held in place in the main body by a shaft collar 18 however any suitable hardware or securing means may be used.

The means of injecting is comprised of an injector arm 13,14 slidably housed in the main body 10 and a manually releasable spring loaded latch 16 providing means for allowing motion of injector arm 13,14 in one direction and preventing injector arm's 13,14 return motion in the opposite direction. The injection arm 13,14 is comprised of a substantially horizontal, planar member 14 with a perpendicular, vertical rack 13 attached to and extending upwards from said horizontal planar member. The substantially horizontal, planar member 14 fits slidably into the hypodermic chamber 12. In the preferred embodiment the teeth of rack 13 are angled upwards however a standard rack tooth arrangement is equally acceptable. The spring loaded latch 16 provides means of snugly and slidably securing injection arm's vertical rack 13 in the device's main body 10 as well as providing means of allowing the rack 13 to slide freely in one direction but prohibiting motion of the rack 13 in the opposite direction. The spring loaded latch 16 has manual thumb release protruding from the lower right side, however the location could be on either or both sides, using any suitable geometry, and protruding in any suitable direction or dimension. The spring loaded latch 16 shown in the preferred embodiment may be replaced by ratchet devices, a pinion gear rotatably mounted to main body 10 in contact with the teeth of rack 13 and connected to a ratchet mechanism, any other suitable latching device, or any other suitable hardware or means of allowing injector arm's 13,14 motion in one direction and not in the opposite direction. Alternatively, the spring loaded latch 16 could be replaced by one skilled in the art in numerous ways by connecting rack 13 via pinions, gears, and ratchet mechanisms directly to pinion 17 in a manner that allows rack 13 to move simultaneously with rack 11 in one direction as pinion 17 is rotated, and preventing the motion of rack 13 in the opposite direction, or reducing the rate of return of rack 13 in the opposite direction relative to the rate of return of rack 11 as pinion 17 is rotated in the opposite direction.

Also shown is an attachment means 19 for attaching the main body 10 of the device to an articulating arm, pole stand, or any other suitable structure providing means for positioning device relative to a patient. The attachment means 19 is only one embodiment and any suitable hardware or means of attachment to a structure suitable for positioning and operating device of current invention may be used.

Figure 2:
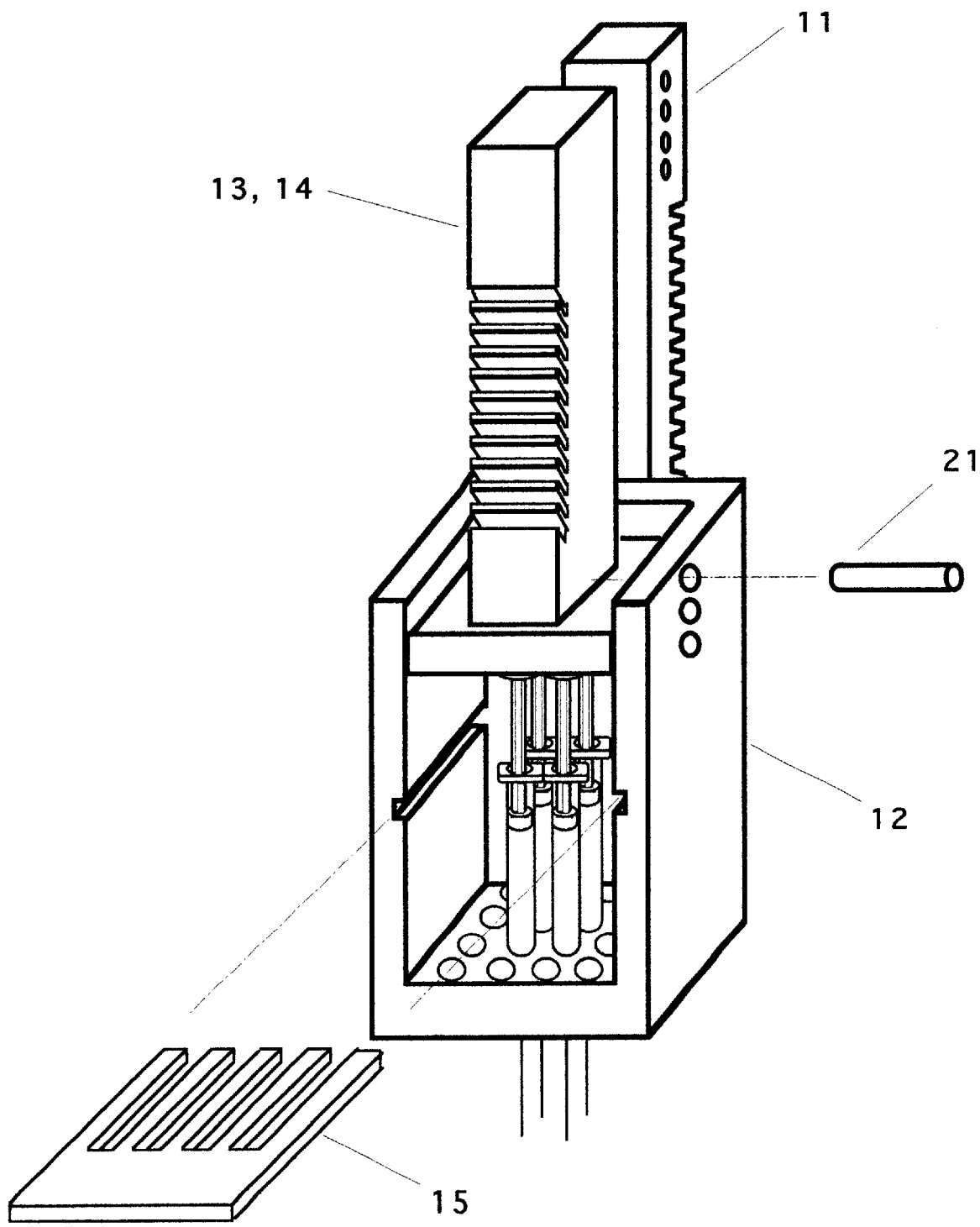
FIG. 2 is a perspective view of the hypodermic chamber with a plurality of hypodermics seated in the device.

FIG. 2 shows a close up view of the chamber 12 with a plurality of hypodermic needles seated in the device.

Figure 3:
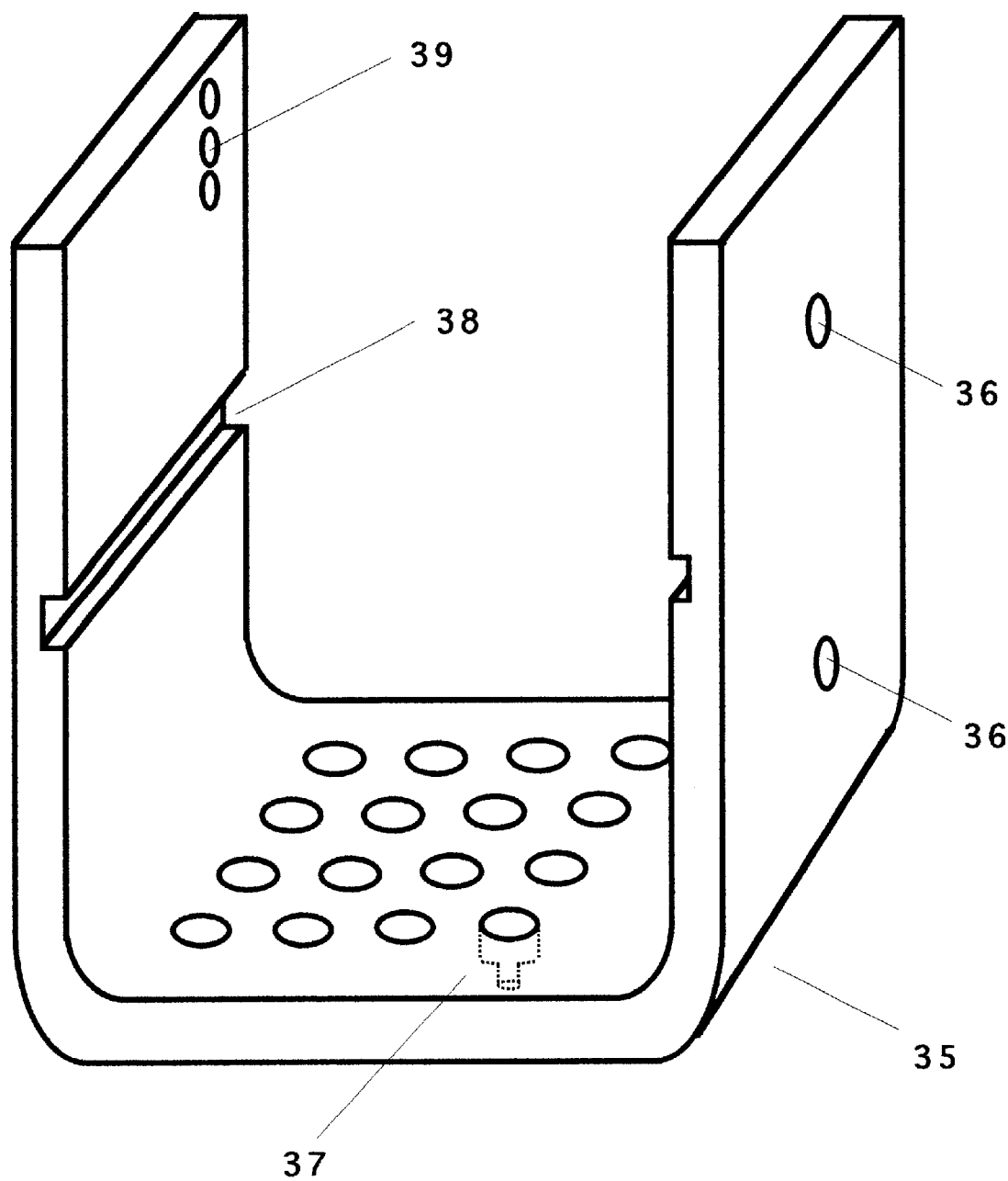
FIG. 3 is an alternate embodiment of hypodermic chamber of the device.

FIG. 3 shows an alternate hypodermic chamber embodiment 35 that may be substituted for hypodermic chamber 12 shown in FIGS. 1 and 2. The alternate hypodermic chamber embodiment 35 is made of a single substantially planar rectangular piece the is bent up at both ends to form a substantially "U" shaped member with a horizontal floor and two perpendicular walls. The horizontal floor has a plurality of orifices 37 for seating hypodermics and the perpendicular walls have a means of accepting 38 the slidable element (15 in FIG. 1). One of the walls also has attachment holes 36 allowing it to be attached to the means of raising and lowering the chamber (11 in FIG. 1) as well as peg holes 39 allowing in to accept a peg (21 in FIG. 1) or pin.

Figures 4A, 4B:
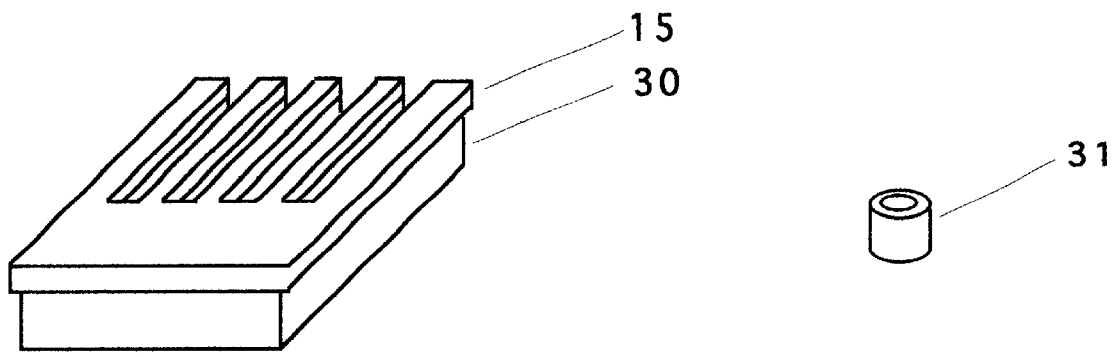
FIGS. 4A, 4B, and 4C are perspective views showing means for self contouring the hypodermics around bone.
Figure 4C:
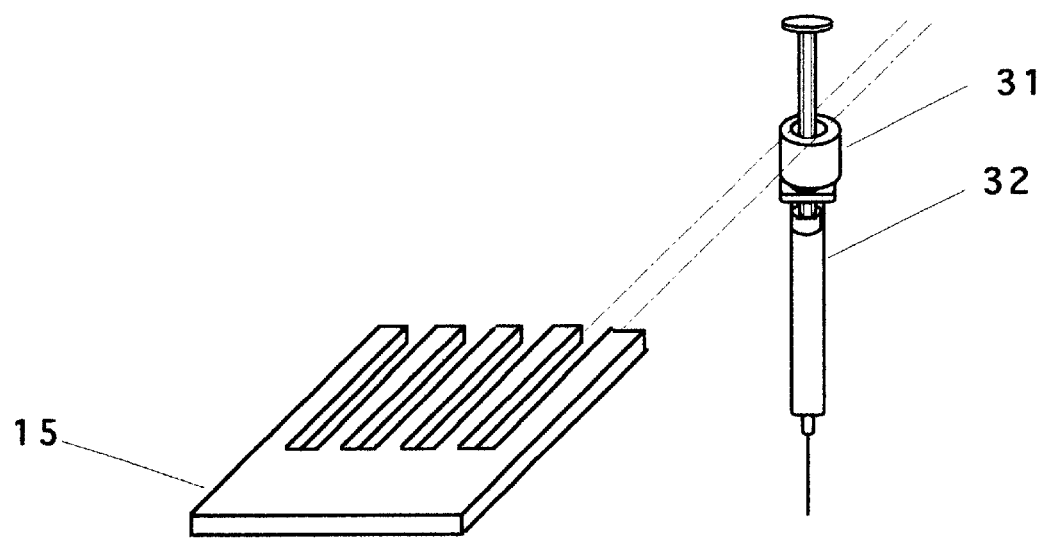

Two means for self contouring of hypodermics are shown in FIGS. 4A,4B, and 4C. FIG. 4A shows a resilient member 30 substantially conforming in shape to the slidable element 15 and attached to the underside of the slidable element 15. The slidable element 15 may he constructed of steel or rigid plastic and the resilient element 30 may be constructed of foam rubber or any suitable resilient material and attached to the underside of slidable element 15 with any suitable adhesive or by any other suitable means. The resiliency of the material may be matched to the application so that the hypodermics are firmly held as the device is being used in the impalement stroke to impale through soft tissue, however if a hard object such as a bone is encountered the resilient element will compress under the stress, preventing the individual hypodermic needle from moving further. Alternatively, FIG. 4B shows a substantially tubular compressible sleeve 31 made of resilient material, and FIG. 4C shows how such a compressible sleeve 31 may be placed on a hypodermic and underneath the slidable element 15 to constitute an alternative embodiment of a self contouring means. Although a compressible sleeve made from a resilient material is shown, springs or any other suitable material or system may be used to provide means of automatically contouring hypodermics around bone or other hard tissue masses.

Figure 5A:
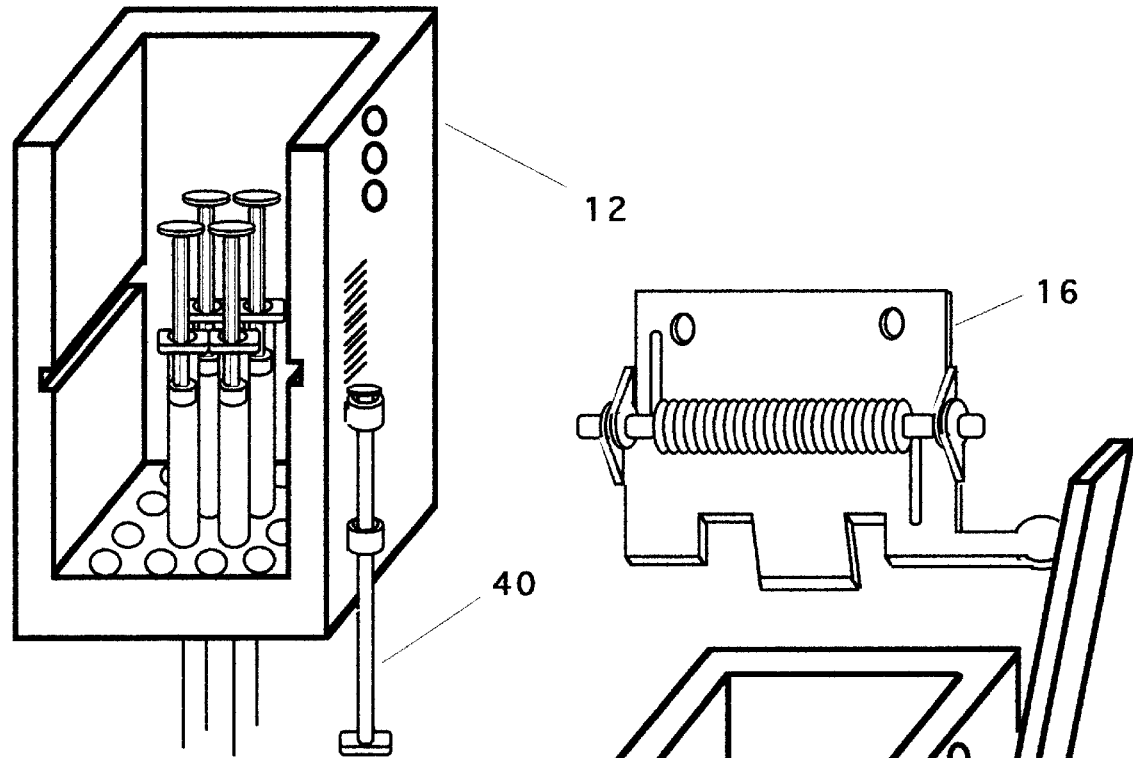
FIGS. 5A and 5B are perspective views showing examples of additional enhancements that may be added to device of present invention.
Figure 5B:
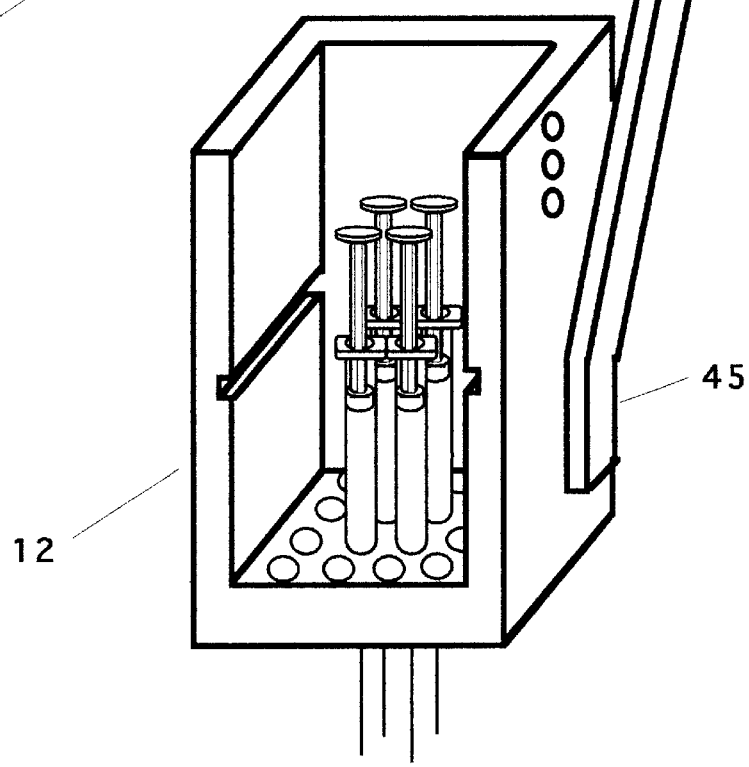

FIGS. 5A and 5B show representative embodiments of enhancements that may be attached to device of current invention to facilitate or automate operation of the device. FIG. 5A shows an impalement/retraction depth measure device comprised of a vertical depth measuring element 40 slidably attached to the side of hypodermic chamber 12 and extending downward to the level of the needles. Measurement markings on the side of the hypodermic chamber 12 wall would show how deep the hypodermics had been impaled during the impalement stroke as well as how far they were still in during the retraction stroke. An operator could use information on the retraction stroke depth to manually disengage the spring loaded latch 16 at a given point before the needles were completely retracted back through the skin. Alternatively, FIG. 5B shows a spring loaded latch 16 disengagement means comprised of a substantially rectangular vertical bar 45 that is bendable horizontally but not appreciably bendable or compressible vertically. The vertical bar 45 is shown in its bent position where it rides on the outside of the thumb release portion of the spring loaded latch 16 as the hypodermic chamber 12 moves downward relative to the stationary spring loaded latch 16. At a certain point in the downward motion of the hypodermic chamber 12, as the vertical bar 45 passes below the spring loaded latch 16 it snaps to a vertical position, parallel to and against the chamber 12 wall. The vertical bar 45 is then in a position to automatically disengage the spring loaded latch 16 by pushing up on the thumb release at a predetermined point in its eventual journey back in the opposite direction (retraction stroke). The above are just a few examples of other features that may be added to device of current invention to enhance functionality or operability and they may be constructed by any suitable means by one skilled in the art. While the above descriptions discuss only two such enhancements, these should not be construed as limitations on the scope of the invention, but rather as an exemplification of possible embodiments. Many other variations and enhancements are possible.

Figure 6:
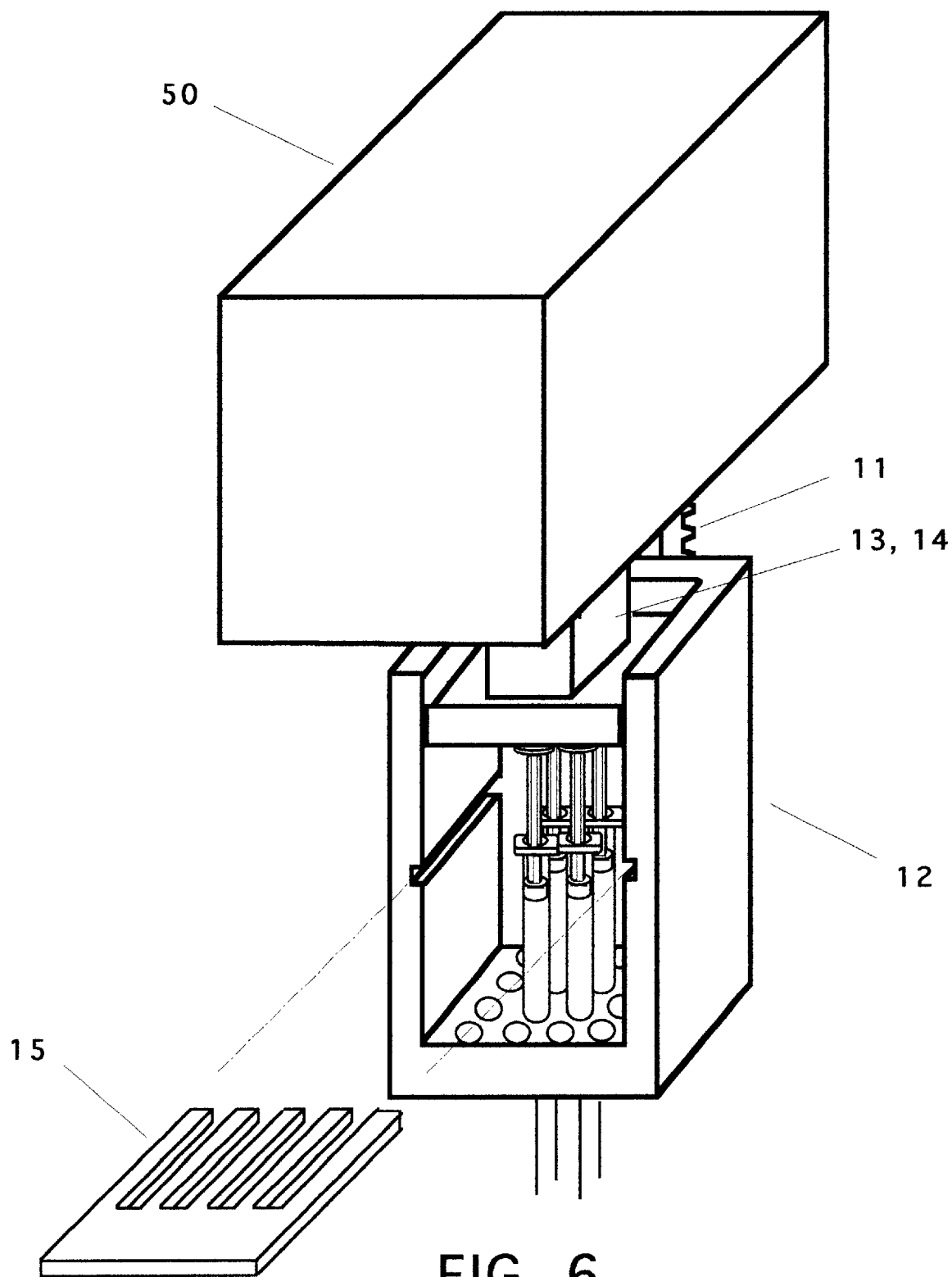
FIG. 6 is a perspective view illustrating another embodiment of present invention with means for automatic operation.

FIG. 6 shows an alternate embodiment with automatic means 50 of providing motion or force to the impalement/retraction rack 11 and injector rack 13. Although 11 and 13 are shown as racks in the preferred embodiment they may be substituted with screw drives, pneumatic cylinders, hydraulics or any other suitable means or mechanism for providing controlled motion for the impalement/retraction of hypodermic chamber 12 and controlled motion or resistance to injector rack or mechanism 13. The means of providing motion or force 50 would contain the necessary mechanisms to accommodate such alternative embodiments and are well established to one skilled in the art. Means of providing motion or force 50 may be microprocessor controlled to allow user definable distance of travel of impalement/retraction rack or mechanism 11, rate of travel of impalement/retraction rack or mechanism 11 in either direction, rate of travel of injector rack or mechanism 13 in either direction, to control the amount of resistance issued to injector rack or mechanism 13 while impalement/retraction rack or mechanism 11 is traveling in either direction, to control the amount of resistance impalement/retraction rack or mechanism 11 is allowed to encounter before it is stopped, or to control any other desired parameter or parameters related to operation of the device of present invention. In a microprocessor controlled version the injector rack or mechanism assembly 13,14,16 may also be replaced by a pump driven pressurized source of therapeutics delivered to a plurality of needles seated in chamber 12, the pressurization being controlled by the microprocessor to coincide with the retraction stroke. Means of providing motion or force 50 may also contain keypads, buttons, or switches for programming or setting parameters of operation, may contain analog or digital displays to show to show parameters that have been set, may contain analog of digital displays to show real time or static readouts of parameter as the machine is being operated or after it has finished, or may contain any other suitable features to facilitate or enhance operation of the device of present invention.

In the preferred embodiment the members of the device are made from plastic or metal however any suitable material may be used. Members of device are held together by screws however any other suitable fasteners, adhesives, or attachment means may be used as well as several pieces cast as one from plastic or metal to resemble the geometry of assemblies previously held together by fasteners.

Operational Description of Invention

The various elements of the invention as shown in FIG. 1 interact as follow. A plurality of hypodermics is filled and seated in the orifices in the floor of hypodermic chamber 12 and the slidable element 15 is inserted into the grooves in the walls of hypodermic chamber securing the main cylindrical bodies of the hypodermics in place while allowing the hypodermic plunger stems to protrude through the top of the slidable element 15. The base of the injector arm 14 is then seated on top of the hypodermic plunger stems and the peg 21 may be inserted through the hypodermic chamber 12 to sit on the top part of the base of injector arm 14 to insure its downward motion with the hypodermic chamber 12. The entire device is positioned appropriately above the area of the patient where the contents of the hypodermics is to be administered. Pulling the lever of the pinion gear 17 forward (out of the page) rotates the pinion gear 17 counter clockwise, which in turn drives the impalement/retraction rack 11 and hypodermic chamber 12 down impaling the seated hypodermics into the patient (impalement stroke) with the injector arm 13,14 also moving freely downward during the impalement stroke. As the lever of the pinion gear 17 is pushed back (into the page) the pinion gear 17 rotates clockwise, which in turn drives the impalement/retraction rack 11 and hypodermic chamber 12 upwards (retraction stroke) and with the spring loaded latch 16 preventing the injector arm's 13,14 return motion the plungers of the hypodermics are forced down during the retraction stroke injecting their contents as they are being pulled out.

Conclusions, Ramifications, and Scope of Invention

The device of the current invention provides a novel means for uniformly delivering drugs to a user defined, three dimensional area within a tissue mass. Examples or drugs that can benefit from such an administered method include, but are not limited to, chemotherapeutics, antibiotics, anti-infectives, substance demonstrating anti-viral or antibacterial activity, cytotoxic substances, or any other suitable class of drugs.

I claim:

1. A device for localized drug perfusion over a three dimensional area inside a tissue mass comprising:
   a) a plurality of vertical substantially planar wall members, each having a lower end attached to a substantially planar horizontal floor member;
   b) said floor member having means of seating a plurality of hypodermic needles and allowing the needles to protrude out through the bottom of said floor member;
   c) said wall members having means of accepting a substantially planar horizontal member,
   d) said substantially planar horizontal member having a plurality of linear, parallel cuts routed out from one side to resemble finger like projections; and
   e) said floor member and/or one said wall member having means of attachment to a means of providing linear motion in a first direction and then providing linear motion in a second opposite direction; and
   f) a means of simultaneously injecting contents of said hypodermic needles as said means of providing linear motion is moving in the second opposite direction.

2. The device of claim 1 wherein said substantially planar horizontal member with finger like projections has a resilient material attached to its underside.

* * * * *